United States Patent

Sipido et al.

Patent Number: 5,552,399
Date of Patent: Sep. 3, 1996

[54] SUBSTITUTED TETRACYCLIC AZEPINE DERIVATIVES

[75] Inventors: Victor K. Sipido, Merksem, Belgium; Francisco J. Fernández-Gadea, Toledo; José I. Andrés-Gil, Madrid, both of Spain; Theo F. Meert, Rumst, Belgium; Pilar Gil-Lopetegui, Toledo, Spain

[73] Assignee: Janssen Pharmaceutica N.V., Beerse, Belgium

[21] Appl. No.: 457,968

[22] Filed: May 31, 1995

[30] Foreign Application Priority Data

Nov. 2, 1994 [EP] European Pat. Off. ............. 94203178

[51] Int. Cl.$^6$ .................. A61K 31/55; C07D 223/20; C07D 498/04; C07D 498/10
[52] U.S. Cl. .................. 514/214; 540/543; 540/576; 540/587
[58] Field of Search .................. 540/576, 543, 540/587; 514/214

[56] References Cited

U.S. PATENT DOCUMENTS 4,039,558  8/1977  Van der Burg et al. ........ 260/326.5 B

FOREIGN PATENT DOCUMENTS

0421823A2  4/1991  European Pat. Off. .

OTHER PUBLICATIONS

Evenson, Moffett. "O–Carbamoyl Oximes as Potential Analgesics," J. Heterocyclic Chem., 17, 351 (1980).

*Primary Examiner*—Philip I. Datlow
*Assistant Examiner*—Anthony Bottino
*Attorney, Agent, or Firm*—Charles J. Metz

[57] ABSTRACT

This invention concerns the compounds of formula (I), the pharmaceutically acceptable salts and stereoisomeric forms thereof, and also the N-oxide forms thereof.

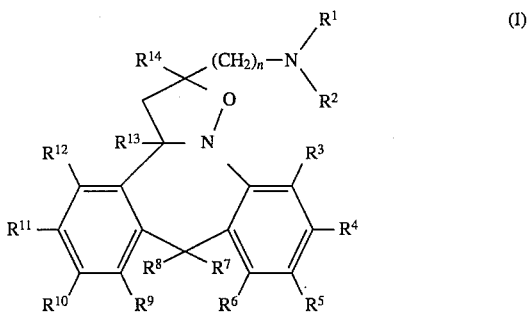

wherein:

$R^1$ and $R^2$ each independently are hydrogen; $C_{1-6}$alkyl; $C_{1-6}$alkylcarbonyl; trihalomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or an optionally substituted heterocycle; $R^3$, $R^4$, $R^5$, $R^6$, $R^9$, $R^{10}$, $R^{11}$ or $R^{12}$ each independently are hydrogen, halo, cyano, hydroxy, trifluoromethyl, trifluoromethoxy, carboxyl, nitro, amino, mono- or di($C_{1-6}$alkyl)-amino, $C_{1-6}$alkylcarbonylamino, aminosulfonyl, mono- or di($C_{1-6}$alkyl)-aminosulfonyl, $C_{1-6}$alkyl, $C_{1-6}$alkyloxy, $C_{1-6}$alkylcarbonyl, $C_{1-6}$alkyloxy-carbonyl; $R^7$ and $R^8$ are each independently hydrogen, hydroxy, $C_{1-6}$alkyl, $C_{1-6}$alkyloxy or $R^7$ and $R^8$ taken together may form mono- or di(cyano)methylene, or together with the carbon atom to which they are attached form a carbonyl or a spiro substituent; or $R^7$ and $R^8$ taken together may form methylene; $R^{13}$ is hydrogen, $C_{1-6}$alkyl, or trifluoromethyl; $R^{14}$ is hydrogen, $C_{1-6}$alkyl, cyano, or trifluoromethyl; n is zero to 6. These compounds were tested as mCPP-antagonists in rats. The compounds of formula (I) may be used as therapeutic agents in the treatment or the prevention of CNS disorders, cardiovascular disorders or gastrointestinal disorders.

22 Claims, No Drawings

SUBSTITUTED TETRACYCLIC AZEPINE DERIVATIVES

CROSS-REFERENCE TO RELATED APPLICATIONS

This application claims priority from EP 94.203.178.2, filed on Nov. 2, 1994.

This invention concerns substituted tetracyclic azepine derivatives having antipsychotic, cardiovascular and gastrokinefic activity and their preparations; it further relates to compositions comprising them, as well as their use as a medicine.

Compounds of similar structure are described in U.S. Pat. No. 4,039,558 which discloses pyrrolidinodibenzo-azepine, -oxazepine, -thiazepine and -diazepine derivatives, having antihistamine, sedative and antidepressant properties. EP-A-0,421,823 describes similar dibenzopyrazino- or benzopyrido-pyrazino-azepine derivatives having anti-allergic and anti-asthmatic activities. The present compounds differ therefrom by the presence of an isoxazolidine ring, and by their pharmacological properties.

This invention concerns compounds of formula (I)

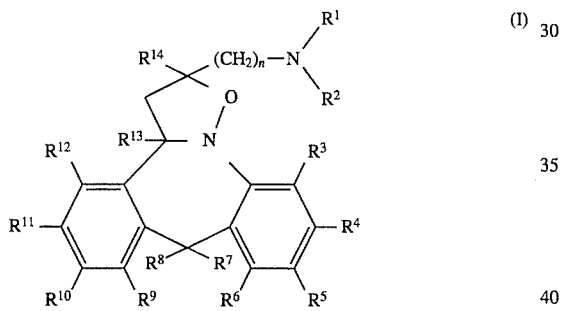

(I)

the pharmaceutically acceptable acid or base addition salts and the stereochemically isomeric forms thereof, and also the N-oxide forms thereof, wherein:

$R^1$ and $R^2$ each independently are hydrogen; $C_{1-6}$alkyl; $C_{1-6}$alkylcarbonyl; trihalomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or a radical of formula:

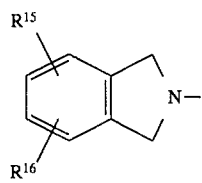 (a)

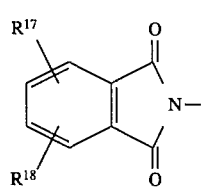 (b)

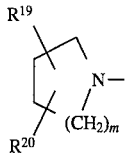 (c)

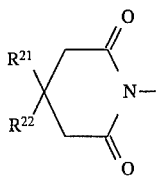 (d)

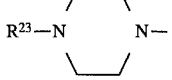 (e)

wherein:

$R^{15}$, $R^{16}$, $R^{17}$ and $R^{18}$ each independently are hydrogen, halo, trifluoromethyl, or $C_{1-6}$alkyl;

m is 1, 2, or 3;

$R^{19}$, $R^{20}$, $R^{21}$ and $R^{22}$ each independently are hydrogen, or $C_{1-6}$alkyl; or $R^{21}$ and $R^{22}$ taken together may form a bivalent radical $C_{4-5}$alkanediyl;

$R^{23}$ is hydrogen; $C_{1-6}$alkyl; $C_{1-6}$alkylcarbonyl; trihalomethylcarbonyl;

$C_{1-6}$alkyloxycarbonyl; aryl; di(aryl)methyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;

$R^3$, $R^4$, $R^5$, $R^6$, $R^9$, $R^{10}$, $R^{11}$ and $R^{12}$ each independently are hydrogen, halo, cyano, hydroxy, trifluoromethyl, trifluoromethoxy, carboxyl, nitro, amino, mono- or di($C_{1-6}$alkyl)amino, $C_{1-6}$alkylcarbonylamino, aminosulfonyl, mono- or di($C_{1-6}$alkyl)aminosulfonyl, $C_{1-6}$alkyl, $C_{1-6}$alkyloxy, $C_{1-6}$alkylcarbonyl, $C_{1-6}$alkyloxycarbonyl; $R^7$ and $R^8$ each independently are hydrogen, hydroxy, $C_{1-6}$alkyl, $C_{1-6}$alkyloxy or $R^7$ and $R^8$ taken together may form mono- or di(cyano)methylene; a bivalent radical of formula $—(CH_2)_2—$, $—(CH_2)_3—$, $—(CH_2)_4—$, $—(CH_2)_5—$, $—O—(CH_2)_2—O—$, $—O—(CH_2)_3—O—$; or, together with the carbon atom to which they are attached, a carbonyl; or $R^7$ and $R^8$ taken together may form methylene;

$R^{13}$ is hydrogen, $C_{1-6}$alkyl or trifluoromethyl;

$R^{14}$ is hydrogen, $C_{1-6}$alkyl, cyano or trifluoromethyl;

n is zero, 1, 2, 3, 4, 5, or 6;

aryl is phenyl; or phenyl substituted with 1, 2 or 3 substituents selected from halo, hydroxy, $C_{1-6}$alkyl and trifluoromethyl.

In the foregoing definitions $C_{1-6}$alkyl defines straight and branch chained saturated hydrocarbon radicals having from 1 to 6 carbon atoms such as, for example, methyl, ethyl, propyl, butyl, 1-methylpropyl, 1,1-dimethylethyl, pentyl, hexyl; $C_{4-5}$alkanediyl defines bivalent straight and branch chained saturated hydrocarbon radicals having from 4 to 5 carbon atoms such as, for example, 1,4-butanediyl, 1,5-pentanediyl; halo is generic to fluoro, chloro, bromo and iodo. The term monocyanomethylene stands for a radical of formula $=CHCN$, and dicyanomethylene for a radical of formula $=C(CN)_2$. In case $R^7$ and $R^8$ taken together form a bivalent radical as defined above, the compounds of formula (I) are spiro compounds.

The pharmaceutically acceptable acid addition salts as mentioned hereinabove are meant to comprise the therapeutically active non-toxic acid addition salt forms which the compounds of formula (I) are able to form. Said salts can be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxyacetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Suitable acids are oxalic acid, in particular (R)- or (S)-malic acid and fumaric acid; especially (S)-malic acid.

The compounds of formula (I) containing acidic protons may also be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Conversely said salt forms can be converted into the free forms by treatment with an appropriate base or acid.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I) are meant to comprise those compounds of formula (I) wherein one or several nitrogen atoms are oxidized to the so-called N-oxide, particularly those N-oxides wherein the nitrogen bearing the $R^1$ and $R^2$ substituents is N-oxidized.

The term "stereochemically isomeric forms" as used hereinbefore and hereinafter defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure. Stereochemically isomeric forms of the compounds of formula (I) and mixtures of such forms are obviously intended to be encompassed by formula (I).

The numbering of the tetracyclic ring-system present in the compounds of formula (I), as defined by Chemical Abstracts nomenclature is shown in formula (I').

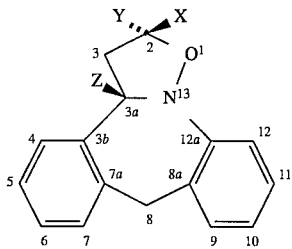

The compounds of formula (I) occur as "cis" and "trans" isomers. Said terms refer to the position of the substituents on the isoxazolidine ring and are in accordance with Chemical Abstracts nomenclature. The nomenclature is unusual in that carbon atom 3b, being part of a cyclic system, is not considered as a relevant substituent of carbon atom 3a. When establishing the configuration, the substituent on carbon atom 3a (i.e. "Z") and the substituent with the highest priority on carbon atom 2 (i.e. either "X" or "Y") are considered. When "Z" and the substituent with the highest priority on carbon atom 2 are on the same side of the mean plane determined by the isoxazolidine ring then the configuration is designated "cis", if not, the configuration is designated "trans".

The compounds of formula (I) have at least two asymmetric centers, namely carbon atom 3a bearing the substituent $R^{13}$ and carbon atom 2 bearing the substituent $R^{14}$. Said asymmetric centers and any other asymmetric center which may be present, are indicated by the descriptors R and S. When a monocyanomethylene moiety is present in the compounds of formula (I), said moiety may have the E- or Z-configuration.

Of some compounds of formula (I) the absolute stereochemical configuration was not experimentally determined. In those cases the stereochemically isomeric form which was first isolated is designated as "A" and the second as "B", without further reference to the actual stereochemical configuration.

Whenever used hereinafter, the term compounds of formula (I) is meant to also include the pharmaceutically acceptable acid addition salts, base addition salts and all stereoisomeric forms, and also the N-oxide forms.

Particular groups of compounds of formula (I) are those wherein one or more of the following restrictions apply:

a) $R^1$ and $R^2$ each independently are hydrogen, $C_{1-6}$alkyl, trihalomethylcarbonyl, $C_{1-6}$alkyl substituted with hydroxy, carboxyl, $C_{1-6}$alkylcarbonyloxy; or $R^1$ and $R^2$ taken together with the nitrogen atom to which they are attached form a radical of formula (a) in which $R^{15}$ and $R^{16}$ are both hydrogen, a radical of formula (b) in which $R^{17}$ and $R^{18}$ are both hydrogen, a radical of formula (c) in which $R^{19}$ and $R^{20}$ are both hydrogen, a radical of formula (d) in which $R^{21}$ and $R^{22}$ taken together form a $C_{4-5}$alkanediyl radical, or a radical of formula (e) in which $R^{23}$ is hydrogen, $C_{1-6}$alkyl, trihalomethylcarbonyl or aryl;

b) $R^3$, $R^4$, $R^5$ and $R^6$ each independently are hydrogen, halo, $C_{1-6}$alkyl, or trifluoromethyl;

c) $R^9$, $R^{10}$, $R^{11}$ and $R^{12}$ each independently are hydrogen, halo, $C_{1-6}$alkyl, or trifluoromethyl;

d) $R^7$ and $R^8$ both are methyl, or in particular hydrogen;

e) $R^{13}$ is methyl, or in particular hydrogen;

f) $R^{14}$ is methyl or cyano, or in particular is hydrogen;

g) n is 1, 2, 3 or 4; and particularly is 1;

h) $R^3$, $R^4$, $R^5$ and $R^6$ each independently are $C_{1-6}$alkyloxy or money- or di($C_{1-6}$alkyl)amino;

i) $R^9$, $R^{10}$, $R^{11}$ and $R^{12}$ each independently are $C_{1-6}$alkyloxy or mono- or di($C_{1-6}$alkyl)amino;

j) $R^7$ is methyl and $R^8$ is hydrogen; or $R^7$ and $R^8$ taken together form methylene.

Of special interest are those compounds of formula (I) or subgroups as defined above, wherein one of the aromatic substituents $R^3$, $R^4$, $R^5$, $R^6$, $R^9$, $R^{10}$, $R^{11}$, $R^{12}$ is selected from hydrogen, halo, $C_{1-6}$alkyl, or trifluoromethyl; the remaining aromatic substituents being hydrogen.

Also of special interest are those compounds of formula (I) or subgroups as defined above, wherein two or more of the aromatic substituents $R^3$, $R^4$, $R^5$, $R^6$, $R^9$, $R^{10}$, $R^{11}$, $R^{12}$ are selected from fluoro, chloro or bromo; the remaining aromatic substituents being hydrogen.

More interesting are those compounds of special interest wherein the aromatic substituents $R^4$, $R^5$ and $R^{11}$ each independently are selected from hydrogen, fluoro, chloro, bromo, methyl or trifluoromethyl; the remaining aromatic substituents being hydrogen.

Preferred compounds are those compounds of formula (I) or subgroups of compounds of formula (I) as defined above, wherein $R^1$ and $R^2$ are both methyl and n is 1 or 2.

Also preferred are those compounds of formula (I) or subgroups of compounds of formula (I) as defined above, wherein $R^1$ is hydrogen, $R^2$ is methyl and n is 1 or 2.

The most preferred compounds are: cis-2,3,3a,8-tetrahydro-N,N-dimethyldibenz[c,f]isoxazolo[2,3-a]azepine-2-methanamine, the stereochemically isomeric forms and pharmaceutically acceptable acid addition salts thereof, and also the N-oxide forms thereof.

Further most preferred are the compounds: cis-2,3,3a,8-tetrahydro-N-methylbenzyl[c,f]isoxazolo[2,3-a]azepine-2-methanamine, the stereochemically isomeric forms and pharmaceutically acceptable acid addition salts thereof, and also the N-oxide forms thereof.

Among the most preferred compounds mentioned hereinabove, (+)-(A-cis)-2,3,3a,8-tetrahydro-N,N-dimethyldibenz[c,f]isoxazolo[2,3-a]azepinemethanamine (S)-hydroxybutanedioate(1:1) is specifically preferred.

The compounds of formula (I) may generally be prepared by a 1,3-dipolar cycloaddition of a dienophile of formula (III) and an intermediate of formula (II). In the intermediates (II) and (III) and in any other intermediate mentioned hereinunder, $R^1$ to $R^{14}$ and n are as defined hereinabove, unless otherwise indicated. Said 1,3-dipolar cycloaddition may conveniently be carded out by mixing the reactants, optionally in a reaction-inert solvent such as, for example, an aromatic solvent, e.g. toluene; a ketone, e.g. 4-methyl-2-pentanone; or a mixture of such solvents. Stirring and elevated temperatures, or increased pressure may enhance the rate of the reaction. The reaction of intermediate (I) with intermediate (III) in practice is regioselective yielding to compounds of formula (I).

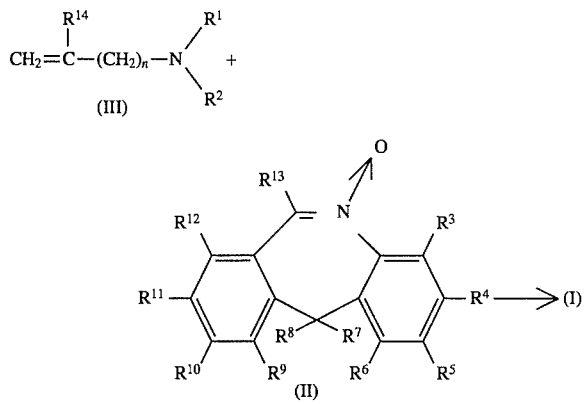

In this and the following preparations, the reaction products may be isolated from the reaction medium and, if necessary, further purified according to methodologies generally known in the art such as, for example, extraction, crystallization, trituration and chromatography.

The compounds of formula (I) may also be converted into each other following art-known transformations. For example, a) a compound of formula (I), wherein $R^1$ and $R^2$ taken together with the nitrogen atom to which they are attached form a radical of formula (b), may be converted into the corresponding primary amine by treatment with hydrazine or aqueous alkali;

b) a compound of formula (I), wherein $R^1$ or $R^2$ is trifluoromethylcarbonyl, may be converted into the corresponding primary or secondary amine by hydrolysis with aqueous alkali;

c) a compound of formula (I), wherein $R^1$ or $R^2$ is $C_{1-6}$alkyl substituted with $C_{1-6}$alkylcarbonyloxy may be hydrolyzed into a compound of formula (I) wherein $R^1$ or $R^2$ is $C_{1-6}$alkyl substituted with hydroxy;

d) a compound of formula (I), wherein $R^1$ and $R^2$ are both hydrogen may be mono- or di-N-alkylated to the corresponding amine form;

e) a compound of formula (I), wherein $R^1$ and $R^2$ are both hydrogen may be N-acylated to the corresponding amide;

f) a compound of formula (I), containing a $C_{1-6}$alkyloxycarbonyl group may be hydrolyzed to the corresponding carboxylic acid.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The intermediates of formula (II) may be prepared by the oxidation of an intermediate of formula (IV) with for example 2-benzenesulfonyl-3-phenyl-oxaziridine, hydrogen peroxide, t-butyl hydroxyperoxide, or metachloroperbenzoic acid.

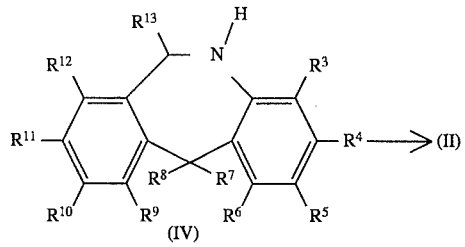

Said oxidation is performed in a reaction-inert solvent at temperatures ranging between −20° C. and 50° C., preferably between 0° C. and room temperature. Suitable solvents are, for example, water, chlofinated hydrocarbons, e.g. dichloromethane or chloroform; aromatic hydrocarbons, e.g. toluene; alcohols such as methanol; ketones, e.g. 4-methyl-2-pentanone; or a mixture of such solvents. When using peroxide oxidants, the reaction rate may be enhanced by using metallic catalysts such as, for example, $Na_2WO_4$, $VO(acetylacetonate)_2$, $Ti(OBu)_4$, or $MoO_2(acetylacetonate)_2$, optionally under a reaction-inert atmosphere such as, for example, argon.

Intermediates of formula (IV) may be formed by the reduction of an imine of formula (V) with hydrogen in combination with a suitable catalyst such as, for example, palladium or platinum supported on for instance charcoal; in a reaction-inert solvent such as, for example,-tetrahydrofuran, methanol or a mixture of such solvents. The formation of an imine of formula (V) is disclosed in J. Chem. Soc. Perk. I (1976), 1279.

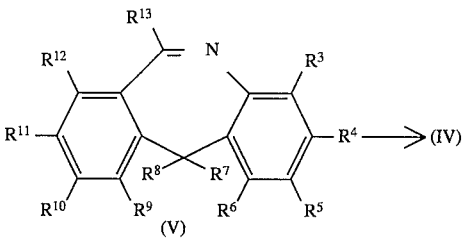

Intermediates of formula (IV) may also be prepared by an intramolecular cyclization of an intermediate of formula (VI) by adding a strong acid such as, for example, sulfuric acid or phosphoric acid, optionally in a reaction-inert solvent, to an intermediate of formula (VI).

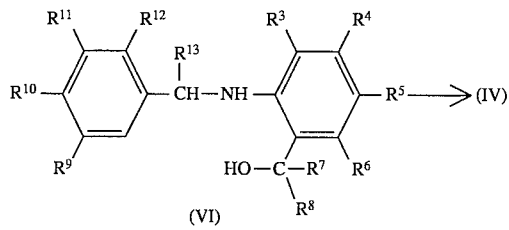

Pure stereochemically isomeric forms of the compounds of formula (I) may be obtained by the application of an-known procedures. Diastereomers may be separated by physical methods such as selective crystallization and chromatographic techniques, e.g. counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid such as, for example, di-1,4-toluolyl-D-tartaric acid, respectively with a suitable chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of the present invention show affinity for 5-$HT_2$ receptors, particularly for 5-$HT_{2A}$ and 5-$HT_{2C}$ receptors (nomenclature as described by D. Hoyer in "Serotonin (5-HT) in neurologic and psychiatric disorders" edited by M. D. Ferrari and published in 1994 by the Boerhaave Commission of the University of Leiden). Furthermore, the compounds of the present invention show interesting pharmacological activity in the "mCPP Test on Rats" which is described hereinafter and in the "Elevated and Illuminated Plus Maze Test" which is described in Drug Dev. Res. 18, 119–144 (1989). Additionally, the present compounds show interesting pharmacological activity in the "Tail Suspension Test", and also in the "LSD Drug Discrimination Test" which is described in Drug Dev. Res. 18, 119–144 (1989). Another interesting property of the compounds of formula (I) is that they suppress amphetamine-induced stereotypical behaviour in rats.

In view of these pharmacological properties, the compounds of formula (I) are useful as therapeutic agents in the treatment or the prevention of central nervous system disorders like anxiety, depression, bipolar disorders, sleep- and sexual disorders, psychosis, schizophrenia, migraine, personality disorders or obsessive-compulsive disorders, social phobias or panick attacks, organic mental disorders, mental disorders in children, aggression, memory disorders and attitude disorders in older people, addiction, obesity, bulimia and similar disorders. In particular, the present compounds may be used as anxiolytics, antidepressants and as agents having the potential to overrule the addictive properties of drugs of abuse.

The compounds of formula (I) may also serve as therapeutic agents in the treatment or the prevention of damage to the nervous system caused by trauma, stroke, neurodegenerative illnesses and the like; cardiovascular disorders like high blood pressure, thrombosis, stroke, and the like; and gastrointestinal disorders like dysfunction of the motility of the gastrointestinal system and the like. The present compounds may also be useful as anticonvulsive agents.

In view of the above uses of the compounds of formula (I), it follows that the present invention also provides a method of treating warm-blooded animals suffering from such diseases, said method comprising the systemic administration of a therapeutic amount of a compound of formula (I) effective in treating the above described disorders.

The present invention thus also relates to compounds of formula (I) as defined hereinabove for use as a medicine, in particular for use as medicine to treat the above described disorders.

Those of skill in the treatment of such diseases could determine the effective therapeutic amount from the test results presented hereinafter. An effective therapeutic amount would be from about 0.001 mg/kg to about 40 mg/kg body weight, more preferably from about 0.003 mg/kg to about 10 mg/kg body weight.

For ease of administration, the subject compounds may be formulated into various pharmaceutical forms for administration purposes. To prepare the pharmaceutical compositions of this invention, a therapeutically effective amount of the particular compound, optionally in addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, offs, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose axe, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Acid or base addition salts of compounds of formula (I) due to their increased water solubility over the corresponding base or acid form, are obviously more suitable in the preparation of aqueous compositions.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carder. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate and not to limit the scope of the present invention.
Experimental part
Hereinunder, "DIPE" means diisopropylether, and "EtOAc" means ethylacetate.
A. Preparation of the intermediates

EXAMPLE 1

Trifluoroacetic acid anhydride (12.7 ml) was added dropwise at 0° C. to a solution of N-methyl-2-propen-1-amine (5 g) and triethylamine (14.7 ml) in diethylether (50 ml) and this mixture was stirred at room temperature for 6 hours, after which the solvent was evaporated. The residue was dissolved in water, extracted with $CH_2Cl_2$ and the solvent evaporated, yielding 9.4 g (75%) of 2,2,2-trifluoro-N-methyl-N-2-propenylacetamide (interm. 1).

Analogously, 1-(2-propenyl)-4-(trifluoroacetyl)piperazine (interm. 2) was prepared.

EXAMPLE 2 a) A mixture of N-methyl-2-propen-1-amine (2.7 ml), ethyl 3-bromo-propanoate (4.5 ml) and potassium carbonate (5.8 g) in 2-butanone (20 ml) was stirred at 50° C. for 4 hours. The mixture was cooled to room temperature, filtered and the filtrate evaporated. The residue was dissolved in water, extracted with $CH_2Cl_2$ and the solvent evaporated. The residue was purified by column chromatography over silica gel (eluent: $CH_2Cl_2/CH_3OH$ 9.75/0.25). The pure fractions were collected and evaporated, yielding 3 g (63%) of ethyl N-methyl-N-2-propenyl-β-alanine (interm. 3).

Similarly, the following intermediates were prepared:

ethyl 4-[methyl(2-propenyl)amino]butanoate (interm. 4); and ethyl 5-[methyl(2-propenyl)amino]pentanoate (interm. 5).

b) A mixture of intermediate 4 (14 g) in a hydrochloric acid solution (35%) (38 ml), acetic acid (38 ml) and water (19 ml) was stirred and refluxed for 5 hours. The mixture was cooled on an ice bath and NaOH (50%) was added until the pH was about 6 after which the solvent was evaporated. The residue was washed with $CH_2Cl_2$. The precipitate was filtered off and the filtrate evaporated. The syrup (19.4 g) was washed with toluene and the solvent was evaporated. The product was used without further purification, yielding 15 g (100%) of 4-[methyl(2-propenyl)amino]butanoic acid (interm. 6).

Analogously, 5-[methyl(2-propenyl)amino]pentanoic acid (interm. 7) was prepared from intermediate 5.

EXAMPLE 3

A mixture of 5-hexen-1-ol (5 g) and 8-azaspiro[4.5]decane-7,9-dione (14 ml) in triethylamine (150 ml) was cooled on an ice bath. Methane-sulfonyl chloride (8.6 g) in triethylamine (50 ml) was added dropwise and the mixture was stirred at room temperature for 1 hour. The mixture was filtered off and the filtrate evaporated. Dichloromethane (7.7 g), potassium carbonate (7.6 g) and N,N-dimethylformamide (100 ml) were added to the residue and the mixture was stirred at 160° C. overnight. The mixture was filtered off and the filtrate evaporated. The residue was purified by short open column chromatography over silica gel (eluent: $CH_2Cl_2/CH_3OH$ 100/0 to 98/2). The pure fractions were collected and evaporated, yielding 1.5 g (13%) of 8-(5-hexenyl)-8-azaspiro[4.5]decane-7,9-dione (interm. 8).

EXAMPLE 4 a) $P_2O_5$ (516.5 g) was added portionwise to $H_3PO_4$ (247.5 ml) and stirred under a $N_2$ flow at room temperature. The mixture was stirred for 2 hours at 120° C., then cooled to 50° C. p-Xylene (1810 ml) was added, and stirring was continued for 15 minutes. $POCl_3$ (83.3 g) was added, and stirring was continued for 10 minutes. N-[2-(phenylmethyl)phenyl]formamide (prepared as described in Helv. Chim. Acta 47(5) 1163–72 (1964)) (37.2 g) was added portionwise. The mixture was stirred for 30 minutes at 60°–70° C. Another portion of N-[2-(phenylmethyl)phenyl]formamide (74.3 g) was added portionwise, and the reaction mixture was stirred overnight at 100° C. The reaction mixture was cooled and the p-xylene layer was removed. Water (990 ml) was added slowly. The mixture was cooled with ice-water. A solution of KOH (1073 g) in water (2200 ml) was added over 2 hours. $CH_2Cl_2$ (500 ml) was added dropwise and the mixture was stirred vigorously during 15 minutes. The organic layer was separated. The aqueous layer was extracted twice with $CH_2Cl_2$. The combined organic layers were dried with $MgSO_4$, filtered off and the solvent evaporated. The residue was purified by distillation yielding a mixed fraction. The mixed fraction was repurified twice by distillation, yielding 1.4 g of 11H-dibenz[b,e]azepine (interm. 9).

b) A mixture of intermediate 9 (116 g) in methanol (1000 ml) was hydrogenated with palladium on activated carbon (10%) (17.7 g) as a catalyst. After uptake of hydrogen (1 eq.), the catalyst was filtered off and the filtrate evaporated. The residue was stirred up in DIPE (80%), the precipitate was filtered off and dried in vacuo at 45° C. for 24 hours, yielding 88.1 g (75.7%) of 6,11-dihydro-5H-dibenz[b,e]-azepine (interm. 10).

In a similar way, there were prepared:
3-chloro-6,11-dihydro-5H-dibenz[b,e]azepine (interm. 11); and
2-chloro-6,11-dihydro-5H-dibenz[b,e]azepine (interm. 12).

c) Bromine (1.3 ml) was added dropwise to a mixture of intermediate 10 (5 g) in acetic acid (12 ml) and the mixture was stirred at room temperature for 4 hours. The solvent was evaporated and the residue was washed with $NH_4OH$ (10%) and dissolved in $CH_2Cl_2$. The organic layer was dried with $Na_2SO_4$, filtered off and evaporated. The residue (8 g) was purified by flash chromatography over silica gel (eluent:hexane/EtOAc 9/1). The pure fractions were collected and evaporated, yielding 4 g (56%) of 2 bromo-6,11-dihydro-5H-dibenz[b,e]azepine (interm. 13).

EXAMPLE 5 a) 2-amino-6-chlorobenzoic acid (25 g) dissolved in acetic anhydride (100 ml) was stirred at 120° C. for 2 hours. The mixture was cooled to room temperature and filtered off. The precipitate was washed with water and $Na_2CO_3$ (10%) and dissolved in $CH_2Cl_2$. The solution was dried with $Na_2SO_4$, filtered off and evaporated. The residue was crystallized twice from benzene, yielding 13 g (46%) of 5-chloro-2-methyl-4H-3,1 -benzoxazin-4-one; mp. 148.7° C. (interm. 14).

b) Intermediate 14 (20 g) was dissolved in tetrahydrofuran (200 ml) and the mixture was cooled on an ice water bath under a $N_2$ atmosphere. Phenylmagnesium bromide (34 ml) in tetrahydrofuran (100 ml) was added dropwise and the mixture was stirred at 10° C. for 1 hour. The mixture was quenched with water and HCl (2N) and extracted twice with $CH_2Cl_2$. The combined organic layers were dried with $Na_2SO_4$, filtered off and the filtrate evaporated. The residue was purified by short open column chromatography over silica gel (eluent:$CH_2Cl_2$). The pure fractions were collected and evaporated, yielding 24.5 g (87%) of N-(2-benzoyl-3-chlorophenyl)-acetamide (interm. 15).

c) Intermediate 15 (20 g) dissolved in acetic acid (700 ml) and hydrochloric acid (175 ml) was stirred and refluxed for 6 hours. The mixture was cooled to room temperature and the solvent evaporated. The residue was partitioned between $CH_2Cl_2$ and $Na_2CO_3$ 10%. The organic layer was dried with $Na_2SO_4$, filtered off and evaporated. The residue was crystallized from DIPE/EtOAc, yielding 10.5 g (62%) of (2-amino-6-chlorophenyl)phenylmethanone; top. 191.5° C. (interm. 16).

d) Intermediate 16 (10.5 g) and hydrazine hydrate (8.8 ml) were dissolved in 1,2-ethanediol (200 ml) and the mixture was stirred at 200° C. for 2 hours. The mixture was cooled to 60° C., KOH (5.1 g) was added and the mixture was stirred at 200° C. overnight. The mixture was cooled to room temperature and partitioned between water and $CH_2Cl_2$. The organic layer was dried with $Na_2SO_4$, filtered off and evaporated, yielding 9 g (90%) of 3-chloro-2-(phenylmethyl)-benzenamine (interm. 17).

e) A mixture of intermediate 17 (10 g) dissolved in formic acid (100 ml) was stirred and refluxed for 2 hours. The mixture was cooled to room temperature and the solvent evaporated. $Na_2CO_3$ (10%) was added to the residue and this aqueous mixture was extracted twice with $CH_2Cl_2$. The organic layer was dried with $Na_2SO_4$, filtered off and evaporated, yielding 9.6 g (85%) of N-[3-chloro-2-(phenylmethyl)phenyl]formamide (interm. 18).

f) Starting from intermediate 18, 1-chloro-6,11-dihydro-5H-dibenz[b,e]azepine (interm. 19) was prepared following the procedures as described in example 4.

Analogously, 6,11-dihydro-4-methyl-5H-dibenz[b,e]azepine (interm. 20) was prepared.

EXAMPLE 6 a) A solution of 3-bromobenzenamine (20 g) in 1,2-dichloroethane was added dropwise under a $N_2$ atmosphere to a solution of $BCl_3$/xylene (128 ml) in 1,2-dichloroethane cooled on ice. Cyanobenzene (12 g) in 1,2-dichloroethane and $AlCl_3$ (17 g) were also added and the mixture was stirred and refluxed overnight. The mixture was cooled, ice/HCl (2N) was added while stirring and the mixture was stirred and heated at 80° C. for 30 minutes. The mixture was cooled, diluted with water and extracted with $CH_2Cl_2$.

The organic layer was dried with $Na_2SO_4$, filtered off and evaporated. The residue was purified by short open column chromatography over silica gel (eluent:hexane/$CH_2Cl_2$/EtOAc 6/3/1). The pure fractions were collected and evaporated, yielding 13 g (41%) of (4-bromo-2-aminophenyl)phenyl-methanone (interm. 21).

b) Starting from intermediate 21, 3-bromo-6,11-dihydro-5H-dibenz[b,e]azepine (interm. 22) was prepared in an analogous manner as intermediate 19 was prepared from intermediate 16 as described in example 5d, 5e and 5f.

Analogously, there were prepared:
6,11-dihydro-3-methyl-5H-dibenz[b,e]azepine (interm. 23);
6,11-dihydro-2-methyl-5H-dibenz[b,e]azepine (interm. 24);
6,11-dihydro-10-methyl-5H-dibenz[b,e]azepine (interm. 25); and
6,11-dihydro-8-methyl-5H-dibenz[b,e]azepine (interm. 26).

EXAMPLE 7

2-[[(4-chlorophenyl)methyl]amino]benzenemethanol (6.7 g) (prepared as described in J. Chem. Soc. Chem. Commun., 1989 (1), 44–5) was cooled under a $N_2$ atmosphere to −40° C. Sulfuric acid (35 ml) was added dropwise keeping the temperature at about −10° C. and the mixture was stirred at room temperature for 1 hour. The mixture was poured into ice water and basified carefully with KOH. The mixture was filtered off and the precipitate was washed with water and $CH_2Cl_2$. The filtrate and the washings were extracted, dried with $Na_2SO_4$, filtered off and evaporated, yielding 5.8 g (95%) of 9-chloro-6,11-dihydro-5H-dibenz-[b,e]azepine (interm. 27).

Analogously, 3-fluoro-6,11-dihydro-5H-dibenz[b,e]azepine (interm. 28) was prepared.

EXAMPLE 8

Procedure 1

3-Phenyl-2-(phenylsulfonyl)oxaziridine (18.7 g) was added portionwise to a solution of intermediate 10 (7 g) in $CHCl_3$ (120 ml) and was subsequently stirred at room temperature for 2 hours. The solvent was evaporated and the residue was purified by short open column chromatography over silica gel (eluent: CH$_2$Cl$_2$/CH$_3$OH 97.5/2.5). The pure fractions were collected and evaporated, yielding 10 g (80%) pounds listed in Table 1 were prepared analogously to procedure 1.

TABLE 1

| Int. No. | R$^3$ | R$^4$ | R$^5$ | R$^6$ | R$^7$ | R$^8$ | R$^9$ | R$^{10}$ | R$^{11}$ | R$^{12}$ | R$^{13}$ | physical data (mp. in °C.) |
|---|---|---|---|---|---|---|---|---|---|---|---|---|
| 29 | H | H | H | H | H | H | H | H | H | H | H | 109.2 |
| 30 | H | Cl | H | H | H | H | H | H | H | H | H | — |
| 31 | H | H | Cl | H | H | H | H | H | H | H | H | — |
| 32 | H | H | H | Cl | H | H | H | H | H | H | H | — |
| 33 | H | Br | H | H | H | H | H | H | H | H | H | — |
| 34 | CH$_3$ | H | H | H | H | H | H | H | H | H | H | — |
| 35 | H | CH$_3$ | H | H | H | H | H | H | H | H | H | — |
| 36 | H | H | CH$_3$ | H | H | H | H | H | H | H | H | — |
| 37 | H | H | H | H | H | H | CH$_3$ | H | H | H | H | — |
| 38 | H | H | H | H | H | H | H | CH$_3$ | H | H | H | — |
| 39 | H | H | H | H | H | H | H | Cl | H | H | H | — |
| 40 | H | F | H | H | H | H | H | H | H | H | H | — |
| 41 | H | H | Br | H | H | H | H | H | H | H | H | — |
| 42 | H | H | H | H | H | H | H | H | H | H | CH$_3$ | 141.7 |
| 43 | H | H | H | H | CH$_3$ | CH$_3$ | H | H | H | H | H | — |
| 44 | H | H | H | CH$_3$ | H | H | H | H | H | H | H | — |
| 45 | H | H | H | H | CH$_3$ | H | H | H | H | H | H | — |
| 46 | H | H | H | F | H | H | H | H | H | H | H | — |
| 47 | H | H | H | H | H | H | F | H | H | H | H | — |
| 48 | H | H | H | H | H | H | H | F | H | H | H | — |
| 49 | H | H | H | H | H | H | H | H | F | H | H | — |
| 50 | H | H | H | H | H | H | H | H | H | F | H | — |
| 51 | H | H | H | H | H | H | H | CF$_3$ | H | H | H | — |
| 52 | H | H | H | H | H | H | H | H | H | CF$_3$ | H | — |
| 53 | H | H | H | H | H | H | Cl | H | H | H | H | — |
| 54 | H | H | H | H | H | H | H | H | Cl | H | H | — |
| 55 | H | Cl | Cl | H | H | H | H | H | H | H | H | — |
| 56 | H | Cl | H | H | H | H | Cl | H | H | H | H | — |
| 57 | H | Cl | H | H | H | H | H | H | Cl | H | H | — |
| 58 | H | Cl | F | H | H | H | H | H | H | H | H | — |
| 59 | H | F | H | H | H | H | Cl | H | H | H | H | — |
| 60 | H | F | H | H | H | H | H | H | Cl | H | H | — |
| 61 | H | F | H | H | H | H | F | H | H | H | H | — |
| 62 | H | F | H | H | H | H | H | H | F | H | H | — |
| 63 | H | Cl | H | H | H | H | Cl | Cl | H | H | H | — |
| 64 | H | Cl | H | H | H | H | H | Cl | Cl | H | H | — |
| 65 | H | H | H | Br | H | H | H | H | H | H | H | — |
| 66 | H | H | H | H | H | H | Br | H | H | H | H | — |
| 67 | H | H | H | H | H | H | H | Br | H | H | H | — |
| 68 | H | H | H | H | H | H | H | H | Br | H | H | — |
| 69 | H | OCH$_3$ | H | H | H | H | H | H | H | H | H | — |
| 70 | H | H | H | OCH$_3$ | H | H | H | H | H | H | H | — |
| 71 | H | H | H | H | H | H | H | H | OCH$_3$ | H | H | — |
| 72 | H | H | H | H | IH | IH | H | N(CH$_3$)$_2$ | H | H | H | — | of 11H-dibenz[b,e]azepine,5-oxide; mp. 109.2° C. (interm. 29).

Procedure 2

A solution of intermediate 10 (50 g) in CH$_2$Cl$_2$ (1282 ml) was stirred and cooled to ±10° C. A solution of metachloroperbenzoic acid (115.6 g) in CH$_2$Cl$_2$ (2430 ml) was added dropwise at <15° C. The reaction mixture was stirred for 1 hour. The mixture was extracted with a 10% aqueous Na$_2$SO$_3$ solution (1 liter), then with a 5% aqueous Na$_2$CO$_3$ solution. The organic phase was dried, filtered, and the solvent was evaporated, yielding 53.5 g (quantitative yield) of 11H-dibenz[b,e]azepine,5-oxide (interm 29).

Analogous to procedure 2, 11-methylene-11H-dibenz[b,c]azepine,5-oxide was prepared (interm. 73). The com- B. Preparation of compounds of formula (I)

EXAMPLE 9

A mixture of intermediate 29 (2.7 g) and N,N-dimethyl-2-propen-1-amine (3 ml) in toluene (60 ml) was stirred at 100° C. overnight. The solvent was evaporated and the residue was purified by flash chromatography over silica gel (eluent: CH$_2$Cl$_2$/CH$_3$OH 95/5). The pure fractions were collected and evaporated. The residue (3.1 g), containing the free base (±)-cis-2,3,3a,8-tetrahydro-N,N-dimethyldibenz[c,f]isoxazolo[2,3-a]-azepine-2-methanamine (comp. 59), was converted into the oxalic acid salt (1:1) in C$_2$H$_5$OH at room temperature, yielding 2.6 g (52%) of (±)-cis-2,3,3a,8-tetrahydro-N,N-dimethyldibenz[c,f]isoxazolo-[2,3-a]azepine-2-methanamine ethanedioate(1:1); mp. 139.5° C. (comp. 1).

EXAMPLE 10

Following the same procedure as in example 9, but using 4-methyl-2-pentanone as solvent, there was prepared (±)-cis-2,3,3a,8-tetrahydro-2-(1-pyrrolidinyl-methyl)dibenz[c,f]isoxazolo[2,3-a]azepine ethanedioate(1:1); mp. 167.2° C. (comp. 2).

EXAMPLE 11

Using the same procedure as in example 9, but stirring the starting materials without solvent in a Parr Pressure Vessel at 100° C. overnight, there was prepared (±)-(cis+trans)-2,3,3a,8-tetrahydro-N,N,3a-trimethyldibenz[c,f]isoxazolo[2,3-a]azepine-2-methanamine (comp. 3).

EXAMPLE 12

Compound 59 (the free base form of compound 1), as prepared in example 9, was converted to the fumarate salt (1:1) by adding dropwise an ethanolic solution of fumaric acid (0.215 g/ml) to a mixture, cooled on an ice-bath, of the free base form in a mixture of ethanol (8 ml) and diethyl-ether (30 ml). The formed precipitate was filtered off and dried in vacuo, yielding 1 g (71%) of (±)-cis-2,3,3a,8-tetrahydro-N,N-dimethyl-dibenz[c,f]isoxazolo[2,3-a]azepine-2-methanamine (E)-2-butenedioate(1:1); mp. 148.9° C. (comp. 4).

EXAMPLE 13 a) Compound 59 (the free base form of compound 1), as prepared in example 9, was separated and purified by column chromatography over a Chiralcel OJ column (Daicel, 250 g, 20 µm, length: 23 cm; detection at 200 nm; flow: 40 ml/min; eluent: hexane/ethanol 80/20; injection volume: 25 ml).

1) The desired (A-cis)-fractions were collected and the solvent was evaporated. The residue (6.8 g) was dissolved in ethanol (50 ml), stirred at room temperature and converted into the oxalic acid salt (1:1) with a solution of oxalic acid (2.94 g) in ethanol (50 ml). The desired compound crystallized out and the precipitate was filtered off and dried, yielding 5.5 g (24.7%) of (+)-(A-cis)-2,3,3a,8-tetrahydro-N,N-diimethyldibenz[c,f]isoxazolo-[2,3-a]azepine-2-methanamine ethanedioate(1:1); mp. 167.0° C. (comp. 5).

2) The desired (B-cis)-fractions were treated in an analogous manner as the (A-cis)-fractions, yielding 3.4 g (15.2%) of (−)-(B-Cis)-2,3,3a,8-tetrahydro-N,N-dimethyldibenz-[c,f]isoxazolo[2,3-a]azepine-2-methanamine ethanedioate(1:1); mp. 152.4° C. (comp. 6).

b) Compound 1, as prepared in example 9, was separated and purified by column chromatography over a Chiralcel OJ column (Daicel, 250 g, 20 µm, length: 23 cm; detection at 200 nm; flow: 40 ml/min; eluent: hexane/ethanol 80/20; injection: compound 1 (0.55 g) was dissolved in n-hexane/ethanol (1:1) (50 ml); injection volume: 20 ml; concentration: 11.00 mg/ml). Two desired fraction groups (1) and (2) were collected and their solvent was evaporated, yielding 0.2 g (47.5%) (A-cis)-2,3,3a,8-tetrahydro-N,N-dimethyldibenz c,f]isoxazolo-[2,3-a]azepine-2-methanamine (comp. 7) and 0.19 g of fraction (2). Fraction (2) contained an impurity (20%) which was separated by reversed-phase column chromatography over RP-Kromasil C-18 (1 inch; eluent: (0.2% NH₄OAc in H₂O)/CH₃OH 30/70). The pure fractions were collected and the organic solvent was evaporated at room temperature. The aqueous residue was extracted with CHCl₃. The separated organic layer was evaporated, yielding 0.110 g (26.1%) (B-cis)-2,3,3a,8-tetrahydro-N,N-dimethyldibenz[c,f]isoxazolo-[2,3-a]azepine-2-methanamine (comp. 8).

EXAMPLE 14

A mixture of (±)-cis-2-[(2,3,3a,8-tetrahydrodibenz[c,f]isoxazolo[2,3-a]azepin-2-yl)methyl]-1H-isoindole-1,3(2H)-dione (4 g), prepared following the procedure of example 1, and hydrazine hydrate (0.5 ml) in ethanol (80 ml) was stirred at 80° C. for 4 hours. The precipitate was filtered off and purified by open column chromatography over silica gel (eluent: CH₂Cl₂/2-propanone 8/2). The pure fractions were collected and evaporated. The residue (1.6 g) was convened into the oxalic acid salt (1:1) in C₂H₅OH at room temperature. The residue (0.8 g) was purified by column chromatography over silica gel (eluent: CH₂Cl₂/CH₃OH 97.5/2.5 to 95/5). The pure fractions were collected and evaporated, yielding 0.6 g (22%) of (±)-cis-2,3,3a,8-tetrahydrodibenz[c,f]isoxazolo-[2,3-a]azepine-2-methanamine (comp. 9).

EXAMPLE 15

A mixture of (±)-cis-2,2,2-trifluoro-N-methyl-N-[(2,3,3a,8-tetrahydrodibenz[c,f]-isoxazolo[2,3-a]azepin-2-yl)methyl]acetamide (4 g), prepared following the procedure of example 9, and sodium hydroxide (1.06 g) in methanol (60 ml) and water (12 ml) was stirred at 60° C. for 3 hours. The solvent was evaporated, the residue was diluted with water and extracted with CH₂Cl₂. The organic layer was dried with Na₂SO₄, filtered off and evaporated. The residue (3.9 g) was purified by short open column chromatography over silica gel (eluent: CH₂Cl₂/CH₃OH 95/5). The pure fractions were collected and evaporated. The residue was convened into the oxalic acid salt (1:1) in C₂H₅OH at room temperature, yielding 3.2 g (82%) of (±)-cis-2,3,3a,8-tetrahydro-N-methyldibenz[c,f]-isoxazolo[2,3-a]azepine-2-methanamine ethanedioate(1:1); mp. 134.0° C. (comp. 10).

EXAMPLE 16

A mixture of intermediate 29 (54.5 g) and N,N-dimethyl-2-propen-1-amine (35.8 g) in toluene (1000 ml) was stirred overnight at 100° C. The solvent was evaporated. The residue was purified by column chromatography over silica gel (eluent: CH₂Cl₂/CH₃OH 97/3). The desired fractions were collected and the solvent was evaporated. The residue was purified and separated into its enantiomers by column chromatography over Chiralcel OJ (eluent: hexane/ethanol 90/10). The pure fractions were collected and the solvent was evaporated. The residue was dissolved in ethanol (100 ml; p.a.) and converted into the (S)-malic acid salt (1:1) by addition of (−)-(S)-malic acid (9 g). The mixture was stirred overnight and the resulting precipitate was filtered off, dried, stirred in ethanol (100 ml), washed with DIPE, and dried, yielding 18.8 g of (+)-(A-cis)-2,3,3a,8-tetrahydro-N,N-dimethyldibenz[c,f]isoxazolo[2,3-a]azepinemethanamine (S)-hydroxybutanedioate(1:1); mp. 154.2° C.; α=50.41° at 20° C. for 100.58 mg in 10 ml methanol (comp. 58).

EXAMPLE 17

A solution of (+)-(R)-malic acid (0.67 g) in ethanol (10 ml) was added to a solution of compound 59 (1.47 g) in ethanol (10 ml), stirred at room temperature. The resulting clear solution was allowed to crystallize out. The precipitate was filtered off and dried (vacuum; 50° C.; 24 hours). This fraction was recrystallized from ethanol (15 ml), filtered off and dried (vacuum; 50° C.), yielding 0.76 g (±)-cis-2,3,3a, 8-tetrahydro-N,N-dimethyldibenz[c,f]isoxazolo[2,3-a] azepinemethanamine (R)-hydroxybutanedioate (1:1) (35.5%); mp. 138.6° C.; α=13.86° at 20° C. for 10.10 mg in 10 ml methanol (comp. 57).

EXAMPLE 18

Compound 58 (2.1 g) was converted into the free base by treatment with aqueous ammonia (at 0° C.). This mixture was extracted with $CH_2Cl_2$ (100 ml). The separated organic layer was dried, filtered and the filtrate was combined with 3-phenyl-2 -(phenylsulfonyl)oxaziridine (1.3 g). This mixture was stirred for 24 hours at room temperature. The solvent was evaporated and the residue was purified by column chromatography over silica gel (eluent: $CH_2Cl_2$/ ($CH_3OH/NH_3$) 90/10). The pure fractions were collected and the solvent was evaporated. The residue was triturated in DIPE, filtered off and dried, yielding 0.85 g (55%) of (A-cis)-2,3,3a,8-tetrahydro-N,N-dimethyldibenz[c,f]isoxazolo[2,3-a]azepinemethanamine,N-oxide monohydrate; mp. 170° C. (comp. 96).

Tables 2 through 6 list compounds that were prepared in a similar way as in one of the hereinabove mentioned examples.

TABLE 2

| Co No | Ex. No | $R^3$ | $R^4$ | $R^5$ | $R^6$ | $R^9$ | $R^{10}$ | $R^{11}$ | $R^{12}$ | physical data (mp. in °C.) |
|---|---|---|---|---|---|---|---|---|---|---|
| 1 | 9 | H | H | H | H | H | H | H | H | (±)-cis/(COOH)₂/139.5 |
| 4 | 12 | H | H | H | H | H | H | H | H | (±)-cis/fumaric acid/148.9 |
| 5 | 13b | H | H | H | H | H | H | H | H | (+)-(A-cis)/(COOH)₂/167.0 |
| 6 | 13b | H | H | H | H | H | H | H | H | (−)-(B-cis)/(COOH)₂/152.4 |
| 7 | 13a | H | H | H | H | H | H | H | H | (A-cis) |
| 8 | 13a | H | H | H | H | H | H | H | H | (B-cis) |
| 57 | 17 | H | H | H | H | H | H | H | H | (−)-cis/(R)-malic acid/138.6 |
| 58 | 16 | H | H | H | H | H | H | H | H | (+)-(A-cis)/(S)-malic acid/154.2 |
| 59 | 9 | H | H | H | H | H | H | H | H | (±)-cis |
| 60 | 17 | H | H | H | H | H | H | H | H | (−)-(A-cis)/[R-(R*,R*)]-2,3-bis[(4-methylbenzoyl)oxy]-butanedioic acid/155.2 |
| 61 | 13a | H | H | H | H | H | H | H | H | (A-trans)/(S)-malic acid/150.9 |
| 62 | 13a | H | H | H | H | H | H | H | H | (B-trans)/(S)-malic acid/148.2 |
| 11 | 9 | Cl | H | H | H | H | H | H | H | cis/(COOH)₂/141.9 |
| 12 | 9 | H | Cl | H | H | H | H | H | H | ±-cis/(COOH)₂/185.3 |
| 13 | 9 | H | H | Cl | H | H | H | H | H | ±-cis/(COOH)₂/172.2 |
| 14 | 9 | H | H | H | Cl | H | H | H | H | cis/(COOH)₂/177.6 |
| 63 | 9 | H | H | H | H | Cl | H | H | H | cis/(COOH)₂/157.5 |
| 24 | 9 | H | H | H | H | H | Cl | H | H | cis/(COOH)₂/171.8 |
| 15 | 9 | H | H | H | H | H | H | Cl | H | cis/(COOH)₂/182.6 |
| 16 | 9 | H | Br | H | H | H | H | H | H | cis/(COOH)₂/170.5 |
| 27 | 9 | H | H | Br | H | H | H | H | H | cis/181.1 |
| 64 | 9 | H | H | Br | H | H | H | H | H | (+)-(A-cis)/73.5 |
| 65 | 9 | H | H | Br | H | H | H | H | H | (−)-(B-cis)/74.1 |
| 66 | 9 | H | H | H | Br | H | H | H | H | cis/(COOH)₂/166.3 |
| 67 | 9 | H | H | H | H | Br | H | H | H | cis/(COOH)₂/158.3 |
| 68 | 9 | H | H | H | H | H | Br | H | H | cis/(COOH)₂/165.0 |
| 69 | 9 | H | H | H | H | H | H | Br | H | cis/90.2 |
| 17 | 9 | CH₃ | H | H | H | H | H | H | H | (cis+trans)/(COOH)₂/172.8 |
| 18 | 9 | H | CH₃ | H | H | H | H | H | H | cis/(COOH)₂/149.4 |
| 19 | 9 | H | H | CH₃ | H | H | H | H | H | cis/(COOH)₂/137.2 |
| 70 | 9 | H | H | H | CH₃ | H | H | H | H | cis/(COOH)₂/174.7 |
| 20 | 9 | H | H | H | H | CH₃ | H | H | H | cis/(COOH)₂/163.1 |
| 21 | 9 | H | H | H | H | H | CH₃ | H | H | cis/(COOH)₂/162.9 |
| 22 | 9 | H | H | H | H | H | H | CH₃ | H | cis/(COOH)₂/158.4 |
| 23 | 9 | H | H | H | H | H | H | H | CH₃ | (cis+trans)/(COOH)₂/189.1 |
| 25 | 9 | H | F | H | H | H | H | H | H | cis/(COOH)₂/172.7 |

TABLE 2-continued

[Structure: tricyclic compound with CH₂-N(CH₃)₂ substituent, isoxazoline ring, and two phenyl rings bearing R³, R⁴, R⁵, R⁶, R⁹, R¹⁰, R¹¹, R¹²]

| Co No | Ex No | R³ | R⁴ | R⁵ | R⁶ | R⁹ | R¹⁰ | R¹¹ | R¹² | physical data (mp. in °C.) |
|---|---|---|---|---|---|---|---|---|---|---|
| 26 | 9 | H | H | F | H | H | H | H | H | cis/(COOH)₂/157.9 |
| 71 | 9 | H | H | H | F | H | H | H | H | cis/(COOH)₂/175.7 |
| 72 | 9 | H | H | H | H | F | H | H | H | cis/(COOH)₂/151.0 |
| 73 | 9 | H | H | H | H | H | F | H | H | cis/(COOH)₂/157.3 |
| 74 | 9 | H | H | H | H | H | H | F | H | cis/(COOH)₂/171.4 |
| 75 | 9 | H | H | H | H | H | H | H | F | cis/(COOH)₂/190.6 |
| 28 | 9 | H | H | H | H | CF₃ | H | H | H | cis/(COOH)₂/165.4 |
| 76 | 9 | H | H | H | H | H | CF₃ | H | H | cis/(COOH)₂/168.1 |
| 29 | 9 | H | H | H | H | H | H | CF₃ | H | cis/(COOH)₂/170.6 |
| 77 | 9 | H | H | H | H | H | H | H | CF₃ | cis/(COOH)₂/176.7 |
| 78 | 9 | H | H | H | OCH₃ | H | H | H | H | cis/(COOH)₂/176.9 |
| 79 | 9 | H | OCH₃ | H | H | H | H | H | H | cis/102.2 |
| 80 | 9 | H | H | H | H | H | H | OCH₃ | H | cis/(COOH)₂/163.2 |
| 81 | 9 | H | H | H | H | H | N(CH₃)₂ | H | H | cis/3/2(COOH)₂/114.9 |
| 82 | 9 | H | Cl | Cl | H | H | H | H | H | cis/110.6 |
| 83 | 9 | H | Cl | H | H | Cl | H | H | H | cis/malic acid/149.7 |
| 84 | 9 | H | Cl | H | H | H | H | Cl | H | cis/(COOH)₂/196.7 |
| 85 | 9 | H | Cl | H | H | Cl | Cl | H | H | cis/(COOH)₂/195.0 |
| 86 | 9 | H | Cl | H | H | H | Cl | Cl | H | cis/(COOH)₂/192.6 |
| 87 | 9 | H | Cl | F | H | H | H | H | H | cis/(COOH)₂/264.3 |
| 88 | 9 | H | F | H | H | Cl | H | H | H | cis/(COOH)₂/182.9 |
| 89 | 9 | H | F | H | H | H | H | Cl | H | cis/(COOH)₂/195.7 |
| 90 | 9 | H | F | H | H | F | H | H | H | cis/(COOH)₂/154.9 |
| 91 | 9 | H | F | H | H | H | H | F | H | cis/(COOH)₂/171.1 |

TABLE 3

[Structure: tricyclic compound with (CH₂)ₙ-NR¹R² substituent, isoxazoline ring, R¹³, R¹⁴ on ring carbon, and two phenyl rings bearing R⁴, R⁷, R⁸, R¹¹]

| Co. No | Ex No | R¹ | R² | R⁴ | R⁷ | R⁸ | R¹¹ | R¹³ | R¹⁴ | n | phys. data (mp. in °C.) |
|---|---|---|---|---|---|---|---|---|---|---|---|
| 3 | 11 | CH₃ | CH₃ | H | H | H | H | CH₃ | H | 1 | (cis+trans) |
| 9 | 14 | H | H | H | H | H | H | H | H | 1 | ±-cis |
| 10 | 15 | H | CH₃ | H | H | H | H | H | H | 1 | ±-cis/(COOH)₂/134.0 |
| 30 | 9 | CH₃ | CH₃ | H | H | H | H | H | H | 2 | ±-cis/(COOH)₂/150.1 |
| 31 | 9 | CH₃ | CH₃ | H | H | H | H | H | H | 3 | ±-cis/(COOH)₂/132.7 |
| 32 | 9 | CH₃ | CH₃ | H | H | H | H | H | H | 4 | ±-cis/(COOH)₂/142.9 |
| 33 | 9 | C₂H₅ | CH₃ | H | H | H | H | H | H | 1 | cis/(COOH)₂/148.4 |
| 34 | 15 | (CH₂)₂-OH | CH₃ | H | H | H | H | H | H | 1 | ±-cis/(COOH)₂/148.6 |
| 35 | 9 | C₂H₅ | C₂H₅ | H | H | H | H | H | H | 1 | ±-cis/(COOH)₂/ |

TABLE 3-continued

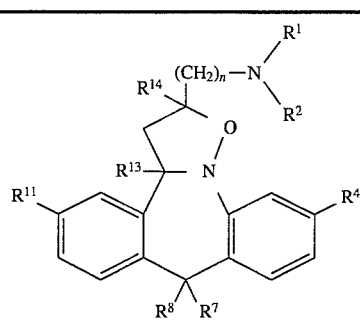

| Co. No | Ex No | R¹ | R² | R⁴ | R⁷ | R⁸ | R¹¹ | R¹³ | R¹⁴ | n | phys. data (mp. in °C.) |
|---|---|---|---|---|---|---|---|---|---|---|---|
| | | | | | | | | | | | 174.0 |
| 36 | 9 | i-C₃H₇ | i-C₃H₇ | H | H | H | H | H | H | 1 | ±-cis/65.8 |
| 37 | 9 | (CH₂)₃-COOH | CH₃ | H | H | H | H | H | H | 1 | ±-cis/130.5 |
| 38 | 9 | (CH₂)₄-COOH | CH₃ | H | H | H | H | H | H | 1 | ±-cis/155.5 |
| 39 | 9 | (CH₂)₂OCOCH₃ | CH₃ | H | H | H | H | H | H | 1 | ±-cis/(COOH)₂/142.6 |
| 92 | 9 | (CH₂)₂OCOCH₃ | CH₃ | Cl | H | H | Cl | H | H | 1 | cis/(COOH)₂/170.5 |
| 40 | 9 | CO—CF₃ | CH₃ | H | H | H | H | H | H | 1 | ±-cis/119.1 |
| 93 | 9 | CH₃ | CH₃ | H | CH₃ | H | H | H | H | 1 | (COOH)₂/128.1 |
| 41 | 9 | CH₃ | CH₃ | H | CH₃ | CH₃ | H | H | H | 1 | cis/(COOH)₂/166.6 |
| 42 | 9 | CH₃ | CH₃ | H | H | H | H | H | CH₃ | 1 | ±-cis/(COOH)₂/165.0 |
| 43 | 9 | CH₃ | CH₃ | H | H | H | H | H | CH₃ | 1 | ±-trans/(COOH)₂/112.2 |
| 94 | 9 | CH₃ | CH₃ | Cl | H | H | Cl | H | CH₃ | 1 | cis/(COOH)₂/199.2 |
| 95 | 9 | CH₃ | CH₃ | Cl | H | H | Cl | H | CH₃ | 1 | trans/67.7 |
| 97 | 9 | CH₃ | CH₃ | H | =CH₂* | H | H | H | H | 1 | ±/(COOH)₂/170.0 |

*R⁷ and R⁸ are taken together

TABLE 4

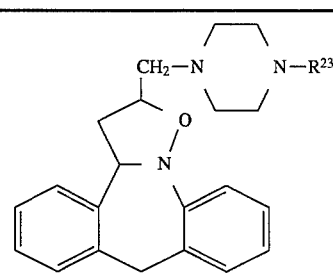

| Co. No. | Ex. No. | R²³ | physical data (mp. in °C.) |
|---|---|---|---|
| 44 | 15 | H | ±-cis/(COOH)₂/278.9 |
| 45 | 9 | CH₃ | ±-cis/(COOH)₂/196.6 |
| 46 | 9 | CO—CF₃ | ±-cis/(COOH)₂/149.4 |
| 47 | 9 | 3-chlorophenyl | ±-cis/59.1 |

TABLE 5

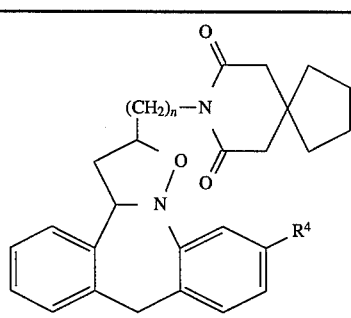

| Co. No. | Ex. No. | R⁴ | n | physical data (mp. in °C.) |
|---|---|---|---|---|
| 48 | 9 | H | 1 | ±-cis/150.8 |
| 49 | 9 | F | 1 | cis/74.7 |
| 50 | 9 | H | 2 | ±-cis/190.0 |
| 51 | 9 | H | 4 | ±-cis |

TABLE 6

$R^{14}$—[structure: bicyclic dibenzo system with CH₂–Q substituent, fused to N-O ring]

| Co. No. | Ex. No. | $R^{14}$ | Q | physical data (mp. in °C.) |
|---|---|---|---|---|
| 2 | 10 | H | 1-pyrrolidinyl | cis/(COOH)₂/167.2 |
| 52 | 9 | H | 1-piperidinyl | ±-cis/(COOH)₂/198.8 |
| 53 | 9 | CN | 1-piperidinyl | ±-trans/127.8 |
| 54 | 9 | H | hexahydro-1H-azepin-1-yl | ±-cis/(COOH)₂/188.0 |
| 55 | 9 | H | 1,3-dihydro-2H-isoindol-2-yl | ±-cis/150.0 |
| 56 | 9 | H | 1,3-dihydro-1,3-dioxo-2H-isoindol-2-yl | ±-cis/184.1 |
| 96 | 18 | H | −N(CH₃)(CH₃)→O | (A-cis) |

C. Pharmacological example

EXAMPLE 19

"mCPP Test on Rats"

Rats were treated with the test compound at a dose varying between 0.0025 mg/kg and 40 mg/kg body weight, at pre-test time T varying between 5 and 480 minutes, and with 1 mg/kg mCPP (metachlorophenylpiperazine), injected intravenously, 15 minutes prior to the test. After pre-test time T elapsed, treated rats were submitted to the "Open Field Test on Rats" as described in Drug Dev. Res. 18, 119–144 (1989), but using an infra-red light source instead of a Kleverlux® (12 V/20 W) light source. A dose at which 40% of the tested rats showed suppression of the mCPP induced effects, i.e. mCPP-antagonism, was defined as an active dose. The activity range of a test compound was measured by the ratio of the HAD (highest active dose) over the LAD (lowest active dose). The compounds with number 1, 4–7, 10, 15, 18, 25, 26, 30, 39, 57, 58, 77, 84, 89 and 91 had a ratio (HAD over LAD) of 16 or more at a pre-test time T being 60 minutes. Also at a pre-test time T of 60 minutes, the compounds with number 2, 8, 11–14, 16, 19, 21, 23, 24, 27, 29, 35, 42–45, 47, 48, 52, 54, 55, 59–62, 65–75, 78, 79, 87, 88, 90 and 92–94 showed mCPP-antagonism at least at one tested dose.

D. Composition examples

"Active ingredient" (A.I.) as used throughout these examples relates to a compound of formula (I), a pharmaceutically acceptable acid addition salt, a stereochemically isomeric form thereof or a N-oxide form thereof.

EXAMPLE 20

ORAL DROPS

500 Grams of the A.I. was dissolved in 0.5 l of 2-hydroxypropanoic acid and 1.5 l of the polyethylene glycol at 60°–80° C. After cooling to 30°–40° C. there were added 35 l of polyethylene glycol and the mixture was stirred well. Then there was added a solution of 1750 grams of sodium saccharin in 2.5 l of purified water and while stirring there were added 2.5 l of cocoa flavor and polyethylene glycol q.s. to a volume of 50 l, providing an oral drop solution comprising 10 mg/ml of A.I. The resulting solution was filled into suitable containers.

EXAMPLE 21

ORAL SOLUTION

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE 22

FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 ml of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 mg of the active ingredient.

Coating

To a solution of 10 grams methyl cellulose gin 75 ml of denaturated ethanol there was added a solution of 5 grams of ethyl cellulose in 150 ml of dichloromethane. Then there were added 75 ml of dichloromethane and 2.5 ml 1,2,3-propanetriol. 10 Grams of polyethylene glycol was molten and dissolved in 75 ml of dichloromethane. The latter solution was added to the former and then there were added 2.5 grams of magnesium octadecanoate, 5 grams of polyvinylpyrrolidone and 30 ml of concentrated colour suspension and the whole was homogenated. The tablet cores were coated with the thus obtained mixture in a coating apparatus.

EXAMPLE 23

INJECTABLE SOLUTION 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

We claim:
1. A compound of the formula:

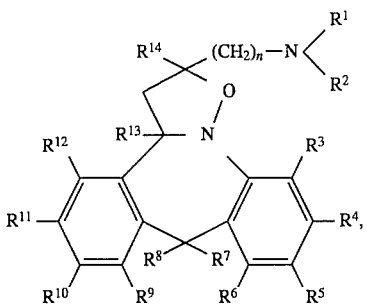

a pharmaceutically acceptable acid or base addition salt thereof, or a stereochemically isomeric form thereof, or an N-oxide form thereof, wherein:

$R^1$ and $R^2$ each independently are hydrogen; $C_{1-6}$alkyl; $C_{1-6}$alkylcarbonyl; trihalomethylcarbonyl; $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl; or $R^1$ and $R^2$ taken together with the nitrogen atom to which they are attached may form a morpholinyl ring or a radical of the formula:

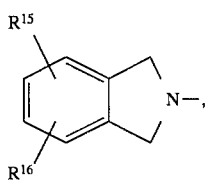 (a)

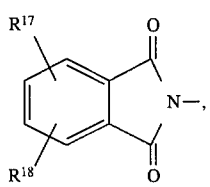 (b)

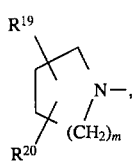 (c)

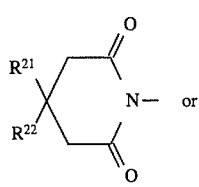 (d)

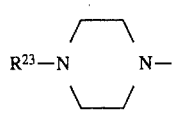 (e)

wherein:
$R^{15}$, $R^{16}$, $R^{17}$ and $R^{18}$ each independently are hydrogen halo, trifluoromethyl or $C_{1-6}$alkyl;

m is 1, 2 or 3;

$R^{19}$, $R^{20}$, $R^{21}$ and $R^{22}$ each independently are hydrogen or $C_{1-6}$alkyl; or $R^{21}$ and $R^{22}$ taken together may form a bivalent radical $C_{4-5}$alkanediyl;

$R^{23}$ is hydrogen; $C_{1-6}$alkyl; $C_{1-6}$alkylcarbonyl; trihalomethylcarbonyl; $C_{1-6}$alkyloxycarbonyl; aryl; di(aryl)methyl; or $C_{1-6}$alkyl substituted with hydroxy, $C_{1-6}$alkyloxy, carboxyl, $C_{1-6}$alkylcarbonyloxy, $C_{1-6}$alkyloxycarbonyl or aryl;

$R^3$, $R^4$, $R^5$, $R^6$, $R^9$, $R^{10}$, $R^{11}$ and $R^{12}$ each independently are hydrogen, halo, cyano, hydroxy, trifluoromethyl, trifluoromethoxy, carboxyl; nitro, amino, mono- or di($C_{1-6}$alkyl) amino, $C_{1-6}$alkylcarbonylamino, aminosulfonyl, mono- or di($C_{1-6}$alkyl) aminosulfonyl, $C_{1-6}$alkyl, $C_{1-6}$alkyloxy, $C_{1-6}$alkylcarbonyl or $C_{1-6}$alkyloxycarbonyl;

$R^7$ and $R^8$ each independently are hydrogen, hydroxy, $C_{1-6}$alkyl, or $C_{1-6}$alkyloxy; or $R^7$ and $R^8$ taken together may form methylene; mono- or di(cyano)methylene; or a bivalent radical of the formula —$(CH_2)_2$—, —$(CH_2)_3$—, —$(CH_2)_4$—, —$(CH_2)_5$—, —O—$(CH_2)_2$—O— or —O—$(CH_2)_3$—O—; or $R^7$ and $R^8$ taken together with the carbon to which they are attached may form a carbonyl;

$R^{13}$ is hydrogen, $C_{1-6}$alkyl or trifluoromethyl;

$R^{14}$ is hydrogen, $C_{1-6}$alkyl, cyano or trifluoromethyl; and n is a number having a value of from 0 to 6, inclusive;

wherein in the foregoing aryl is phenyl or phenyl substituted with 1, 2 or 3 substituents selected from the group consisting of halo, hydroxy, $C_{1-6}$alkyl and trifluoromethyl.

2. A compound according to claim 1, wherein $R^7$ and $R^8$ each independently are hydrogen or methyl, or wherein $R^7$ and $R^8$ are taken together to form methylene.

3. A compound according to claim 2, wherein $R^{13}$ is hydrogen or methyl.

4. A compound according to claim 3, wherein $R^{14}$ is hydrogen, cyano or methyl.

5. A compound according to claim 4, wherein the aromatic substituents $R^4$, $R^5$ and $R^{11}$ each independently are selected from hydrogen, fluoro, chloro, bromo, methyl or trifluoromethyl; the remaining aromatic substituents being hydrogen.

6. A compound according to claim 5, wherein n is 1 or 2, $R^1$ is hydrogen or methyl and $R^2$ is methyl.

7. A compound according to claim 1, wherein the compound is cis-2,3,3a,8-tetrahydro-N,N-dimethyldibenz[c,f]isoxazolo[2,3-a]azepine-2-methanamine; or cis-2,3,3a,8-tetrahydro-N-methyldibenz[c,f]isoxazolo[2,3-a]azepine-2-methanamine, the stereochemically isomeric forms thereof and their pharmaceutically acceptable acid addition salts, and also their N-oxide forms.

8. A compound of formula

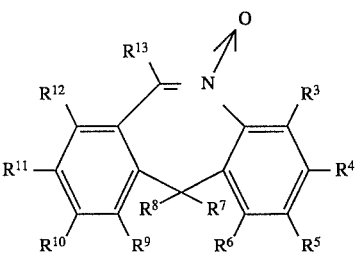

wherein $R^3$ to $R^{13}$ are defined as in claim 1, an acid or base addition salt thereof or a stereochemically isomeric form thereof.

9. A composition comprising a pharmaceutically acceptable carrier and, as active ingredient, a therapeutically effective amount of a compound as defined in claim 1.

10. A composition comprising a pharmaceutically acceptable carrier and, as active ingredient, a therapeutically effective amount of a compound as defined in claim 2.

11. A composition comprising a pharmaceutically acceptable carrier and, as active ingredient, a therapeutically effective amount of a compound as defined in claim 3.

12. A composition comprising a pharmaceutically acceptable carrier and, as active ingredient, a therapeutically effective amount of a compound as defined in claim 4.

13. A composition comprising a pharmaceutically acceptable carrier and, as active ingredient, a therapeutically effective amount of a compound as defined in claim 5.

14. A composition comprising a pharmaceutically acceptable carrier and, as active ingredient, a therapeutically effective amount of a compound as defined in claim 6.

15. A composition comprising a pharmaceutically acceptable carrier and, as active ingredient, a therapeutically effective amount of a compound as defined in claim 7.

16. A method for the treatment of central nervous system disorders selected from the group consisting of psychosis, schizophrenia, migraine, anxiety, depression, and addiction to drugs of abuse, which comprises administering a therapeutically effective amount of a compound as defined in claim 1.

17. A method for the treatment of central nervous system disorders selected from the group consisting of psychosis, schizophrenia, migraine, anxiety, depression, and addiction to drugs of abuse, which comprises administering a therapeutically effective amount of a compound as defined in claim 2.

18. A method for the treatment of central nervous system disorders selected from the group consisting of psychosis, schizophrenia, migraine, anxiety, depression, and addiction to drugs of abuse, which comprises administering a therapeutically effective amount of a compound as defined in claim 3.

19. A method for the treatment of central nervous system disorders selected from the group consisting of psychosis, schizophrenia, migraine, anxiety, depression, and addiction to drugs of abuse, which comprises administering a therapeutically effective amount of a compound as defined in claim 4.

20. A method for the treatment of central nervous system disorders selected from the group consisting of psychosis, schizophrenia, migraine, anxiety, depression, and addiction to drugs of abuse, which comprises administering a therapeutically effective amount of a compound as defined in claim 5.

21. A method for the treatment of central nervous system disorders selected from the group consisting of psychosis, schizophrenia, migraine, anxiety, depression, and addiction to drugs of abuse, which comprises administering a therapeutically effective amount of a compound as defined in claim 6.

22. A method for the treatment of central nervous system disorders selected from the group consisting of psychosis, schizophrenia, migraine, anxiety, depression, and addiction to drugs of abuse, which comprises administering a therapeutically effective amount of a compound as defined in claim 7.

* * * * *